(12) United States Patent
Godik

(10) Patent No.: US 6,192,262 B1
(45) Date of Patent: *Feb. 20, 2001

(54) METHOD OF LIVING ORGANISM MULTIMODAL FUNCTIONAL MAPPING

(75) Inventor: Eduard E. Godik, Suffern, NY (US)

(73) Assignee: DOBI Medical Systems, LLC, Mahwah, NJ (US)

(*) Notice: Under 35 U.S.C. 154(b), the term of this patent shall be extended for 0 days.

This patent is subject to a terminal disclaimer.

(21) Appl. No.: 09/353,891

(22) Filed: Jul. 15, 1999

Related U.S. Application Data

(63) Continuation-in-part of application No. 09/238,404, filed on Jan. 26, 1999, now abandoned, which is a continuation of application No. 08/529,408, filed on Sep. 18, 1995, now Pat. No. 5,865,743, which is a continuation of application No. 08/201,105, filed on Feb. 23, 1994, now abandoned.

(51) Int. Cl.$^7$ .................................................. A61B 5/05
(52) U.S. Cl. ........................................................ 600/407
(58) Field of Search .................... 600/407, 473, 600/475, 476, 477, 310, 425, 430, 437, 438

(56) References Cited

U.S. PATENT DOCUMENTS

| | | | |
|---|---|---|---|
| 3,878,392 | 4/1975 | Yew et al. | 250/306 |
| 3,897,150 | 7/1975 | Bridges et al. | 356/5 |
| 4,207,901 | 6/1980 | Nigam | 128/660 |
| 4,212,306 | 7/1980 | Mahumud | 128/665 |
| 4,281,645 | 8/1981 | Jöbsis | 128/633 |
| 4,286,602 | 9/1981 | Guy | 128/665 |
| 4,312,357 | 1/1982 | Andersson et al. | 128/664 |

(List continued on next page.)

FOREIGN PATENT DOCUMENTS

| | | |
|---|---|---|
| 0099756 | 2/1984 | (EP) . |
| 0108617 | 5/1984 | (EP) . |
| 0140633 | 5/1985 | (EP) . |
| 0447708A3 | 9/1991 | (EP) . |
| 14032241 | 8/1975 | (GB) . |
| 1533648 | 12/1989 | (SU) . |
| 1641268 | 4/1991 | (SU) . |
| WO79/00594 | 8/1979 | (WO) . |
| WO 91/06244 | 5/1991 | (WO) . |
| WO93/11703 | 6/1993 | (WO) . |
| WO94/07408 | 4/1994 | (WO) . |
| WO94/28795 | 12/1994 | (WO) . |

OTHER PUBLICATIONS de Haller EB and Depeursinge C. Simulation of time–resolved breast transillumination. *Medical & Biological Engereering & Computing* 1993; 31:165–70.*

Gandjbakche AH, Nossal R, and Bonner RF. Resolution limits for optical transillumination of abnormalities deeply embedded in tissues. *Medical Physics* 1994; 21:185–91.

Hebden JC and Kruger, RA. Transillumination imaging performance: A time–of–flight imaging system. *Medical Physics* 1990; 17:351–6.

(List continued on next page.)

*Primary Examiner*—Brian L. Casler
(74) *Attorney, Agent, or Firm*—Perkins, Smith & Cohen, LLP; Jacob N. Erlich; Jerry Cohen

(57) ABSTRACT

A method of diagnosing a living organism by analyzing at least two physical parameters of a region under investigation of the living organism in order to provide a multimodal approach to living organism diagnosis. By utilizing information derived from the plurality of physical parameters to generate a series of functional maps, and by, in some instances, applying external influences to the living organism, accurate diagnosis of the living organism can take place.

16 Claims, 1 Drawing Sheet

U.S. PATENT DOCUMENTS

| | | | |
|---|---|---|---|
| 4,328,809 | 5/1982 | Hirschowitz et al. | 600/407 |
| 4,385,634 | 5/1983 | Bowen | 128/653 |
| 4,434,799 | 3/1984 | Taenzer | 128/660 |
| 4,495,949 | 1/1985 | Stoller | 128/664 |
| 4,515,165 | 5/1985 | Carroll | 128/664 |
| 4,536,790 | 8/1985 | Kruger et al. | 358/111 |
| 4,570,638 | 2/1986 | Stoddart et al. | 128/665 |
| 4,573,472 | 3/1986 | Ito | 128/399 |
| 4,576,173 | 3/1986 | Parker et al. | 128/633 |
| 4,583,869 | 4/1986 | Chive et al. | 374/122 |
| 4,616,657 | 10/1986 | Stoller | 128/664 |
| 4,649,275 | 3/1987 | Nelson et al. | 250/358.1 |
| 4,767,928 | 8/1988 | Nelson et al. | 250/341 |
| 4,774,961 | 10/1988 | Carr | 128/736 |
| 4,798,209 | 1/1989 | Klingenbeck et al. | 128/653 |
| 4,807,637 | 2/1989 | Bjorkholm | 128/664 |
| 4,810,875 | 3/1989 | Wyatt | 250/227 |
| 4,817,038 | 3/1989 | Knoll et al. | 364/413.24 |
| 4,817,622 | 4/1989 | Pennypacker et al. | 128/664 |
| 4,829,184 | 5/1989 | Nelson et al. | 250/358.1 |
| 4,862,894 | 9/1989 | Fujii | 128/666 |
| 4,927,244 | 5/1990 | Bahr et al. | 350/350 S |
| 4,945,239 | 7/1990 | Wist et al. | 250/358.1 |
| 4,948,974 | 8/1990 | Nelson et al. | 250/358.1 |
| 4,955,383 | 9/1990 | Faupel | 128/653 R |
| 4,995,398 | 2/1991 | Turnidge | 128/668 |
| 5,079,698 | 1/1992 | Grenier et al. | 364/413.13 |
| 5,099,848 | 3/1992 | Parker et al. | 128/661.07 |
| 5,139,025 | 8/1992 | Lewis et al. | 128/665 |
| 5,170,119 | 12/1992 | Sekihara et al. | 324/260 |
| 5,197,470 | 3/1993 | Helfer et al. | 128/634 |
| 5,213,105 | 5/1993 | Gratton et al. | 128/664 |
| 5,222,495 | 6/1993 | Clarke et al. | 128/633 |
| 5,269,325 | 12/1993 | Robinson et al. | 128/653.1 |
| 5,293,873 | 3/1994 | Fang | 128/664 |
| 5,301,681 | 4/1994 | DeBan et al. | 128/736 |
| 5,303,026 | 4/1994 | Strobl et al. | 356/318 |
| 5,305,748 | 4/1994 | Wilk | 128/653.1 |
| 5,307,807 | 5/1994 | Valdes Sosa et al. | 128/653.1 |
| 5,309,907 | 5/1994 | Fang et al. | 128/633 |
| 5,311,018 | 5/1994 | Zana et al. | 250/330 |
| 5,313,941 | 5/1994 | Braig et al. | 128/633 |
| 5,333,610 | 8/1994 | Hirao | 128/633 |
| 5,337,745 | 8/1994 | Benaron | 128/633 |
| 5,371,368 | 12/1994 | Alfano et al. | 250/341.1 |
| 5,392,210 | 2/1995 | Scholz | 364/413.01 |
| 5,402,782 | 4/1995 | Lodder | 128/653.1 |
| 5,515,847 | 5/1996 | Braig et al. | 128/633 |
| 5,572,996 | 11/1996 | Doiron et al. | 128/633 |
| 5,699,797 | 12/1997 | Godik | 128/653.1 |
| 5,730,133 | 3/1998 | Godik | 128/653.1 |
| 5,747,789 | 5/1998 | Godik | 250/208.1 |
| 5,803,082 | 9/1998 | Stapleton et al. | 128/653.1 |
| 5,865,167 | 2/1999 | Godik | 128/133 |
| 5,865,743 | 2/1999 | Godik | 600/407 |
| 6,002,958 | 12/1999 | Godik | 600/407 |

OTHER PUBLICATIONS

Levin DC, Schapiro RM, Boxt LM, Dunham L, Harrington DP, and Ergun DL. Digital subtraction angiography: principles and pitfalls of image improvement techniques. AJR 1984; 143:447–454.

Sabel M, Horst A. Recent developments in breast imaging (Review). *Physics in Medicine and Biology* 1996; 41:315–68.**

Sickles EA. Breast CT scanning, heavy–ion mammography, NMR imaging, and diaphanography. In Feig SA and McLelland R eds. *Breast Carcinoma: Current Diagnosis and Treatment* 1983; New York: Masson, 233–50.

Godik, E.E., Guljaev, Yu.V., "The Human Being Through 'Eyes of Radiophysics'", *Journal of Radio Engineering* (Russian) 1991, No. 8, pp. 51–62.

Ring, E.F.J. and Hughes, H. "Real Time Video Thermography", in *Recent Developments in Medical and Physiological Imaging* a supplement to *Journal of Medical Engineering and Technology*, 1986, pp. 86–89.

Platonov, S.A., . . . , Godik, E.E., "Informative Tasks of Functional Mapping of Biological Subjects", *Journal of Radio Engineering* (Russian) 1991, No. 8, pp. 62–68. (See English translation "Software Problems of Biological Objects").

Jacquez, J.A. et al., "Spectral Reflectance of Human Skin in the Region 235–1000 nm", *Journal of Applied Physiology*, 1955, vol. 7, No. 3, pp. 523–528.—copy not available.

"Physics of Image Visualization in Medicine", C. Webb, ed. vol. 2, pp. 241–243.—copy not available.

Krenkel, T.E., Kogan, A.G. and Tatatorian, A.M., "Personal Computers in Engineering", Izd. Mir, RiS, (Russian) 1989, p. 71.—copy not available.

Dgagupov, R.G. and Erofeev, A.A., *Piezo–Ceramic Elements in Instrument Designing and Automatics*, Leningrad Izd. Mashinosroenie, 1986, pp. 154–155 (Russian).—copy not available.

Svechnikov S.V. "Optoelectronics elements", Moscow, Izd. "Sov. Radio" 1971, p. 250–256.—copy not available.

Legett, Kate, *Optical mamography offers promise as alternative to x–ray detection*, Biophotonics International, Jan./Feb., 1996, pp. 56–57.—copy not available*.

Godik, Eduard E. and Gulyaev, Uri, V., "Functional Imaging of the Human Body," *IEEE Engineering in Medicine and Biology*, Dec. 1991, pp. 21–29.

*Physics of image visualization in medicine*, C. Webb, ed., vol. 2, p. 382, Moscow, Mir, 1991 (Translated from English) (copy not available).

The comparison of the sensitivity of ultrasound echo and shadow methods for determination of calcification of breast tissues, Proc. Conf. Ultrasound Biology & Medicine—Ubiomed. VI, Warsaw–Jablonna, Sep. 19–23, 1983, pp. 41–49 (copy not available).

Icimury, A. Wave propagation and scattering in randomly inhomogeneous media, vol. 1, pp. 74–79, Moscow, Mir, 1981 (Translated from English) (copy not available).

Barabanenkov, Yu. N. On the relative increase in radiation extinction length due to correlation of weak scatterers, USSR Academy of Sci. Proceedings, Physics of atmosphere and ocean, vol. 18, No. 7, pp. 720–726, 1982 (copy not available).

Vartapetjan, M.A. et al. Sensor perception. An investigation experience with the help of focused ultrasound, Leningrad, Nauka, 1985 (Russian)—copy not available.

Biophysical approach to the problem of safety under the ultrasound diagnostics, Proc. Conf. Ultrasound Biology & Medicine—Ubiomed. YI, Warsaw—Jablonna, Sep. 19–23, pp. 95–99, 1983 (copy not available).

Titce, U. and Shenck, K. Semiconductor scheme technology, p 144, Moscow, Mir, 1982 (Translated from English to Russian) (copy not available).

Krenkel, T.E. et al. *Personal computers in engineering practices*, pp. 71–75, Moscow, RiS, 1989 (Russian) (copy not available).

Guljaev, Yu.V., Godik, E.E. et al. *On the possibilities of the functional diagnostics of the biological subjects via their temporal dynamics of teh infrared images*, USSR Academy Nauk Proceedings/Bophysics—1984, vol. 277, pp. 1486–1491 (copy not available).

Hasset, J. *Introduction into psycho–physiology*,—Moscow, Mir, 1981 (Translated into Russian) (copy not available).

Godik, E.E., Guljaev, Yu.V. *Human and animal physical fields*, V mire nauki (Russian version of Scientific American)/ 1990, No. 5, pp. 74–83 (copy not available).

Marks, F.A. et al., A comprehensive approach to breast caner detection using light . . . , SPIE, vol. 1888, pp. 500–510, Sep. 1993.*

METHOD OF LIVING ORGANISM MULTIMODAL FUNCTIONAL MAPPING

CROSS REFERENCE TO RELATED APPLICATIONS

This application is a continuation in-part of co-pending U.S. application Ser. No. 09/238,404 filed Jan. 26, 1999, now abandoned, entitled METHOD OF LIVING ORGANISM MULTIMODAL FUNCTIONAL MAPPING which in turn is a continuation of U.S. application Ser. No. 08/529,408 filed Sep. 18, 1995 entitled METHOD OF LIVING ORGANISM MULTIMODAL FUNCTIONAL MAPPING and now U.S. Pat. No. 5,865,743, which in turn is a continuation of Ser. No. 08/201,105 filed Feb. 23, 1994, now abandoned, all by the present inventor.

BACKGROUND OF THE INVENTION

The present invention belongs to the field of physics and medicine or, more precisely, to methods and systems or characterizing and investigating the functional state of living organisms and the functional dynamics of the physiological processes taking place during the living organism's vital activity, and using information obtained therefrom in a multimodal approach.

Living organism functional mapping reveals the earliest signs of pathologies on the basis of the integral picture of the organism's functioning. This opens up the possibility of avoiding radical methods of treatment which become necessary when such pathologies are revealed at a later stage of their development. That is why the methods related to the living organism's early functional diagnostics are very promising for the population screening and for development of preventive medicine.

For a long time, functional diagnostics of a living organism's state was performed only with the use of various tests which determined the quality and/or the reaction rates of the organism's physiological systems. Such tests made it possible to only estimate the functional state of the living organism's system when the organism was involved in some purposeful activity. Since the overall picture of the organism functioning was not investigated, such measurements did not give rise to the possibility of performing early diagnosis of pathology.

Only lately, when modern radio physics (electromagnetic theory) methods were applied to biomedical research, the possibility appeared of recording a complex picture of the spatial-temporal dynamics of a living organism's physical fields and radiations, yielding important information on the state of the organism's various regulative systems and organs in the course of natural vital activity.

The human body or organism is a dynamic self-regulative system.

Its stability (homeostasis) is provided by the continuous functioning of different physiological systems. Variations in the organism's physiological parameters result in changes of the biological tissue's physical parameters, such as, for example, the temperature, dielectric permeability, magnetic susceptibility, electric impedance and potentials, currents, etc. The organism's functional dynamics are reflected in the above mentioned dynamic distributions of its physical parameters. Information on the functional dynamics are revealed in the real time scale by the dynamics of the organism's physical fields and radiations: infrared (IR), microwave, acoustical, optical radiations, electric and magnetic fields. Under these conditions, external fields and radiations become parametrically modulated, with those of natural origin such as geomagnetic, electric, light, etc., being first observed.

Different methods of investigating and diagnosing a living organism's state which employ recording the above mentioned physical parameters are known.

For example, to determine the biological tissues' temperature, the tissue's own electromagnetic thermal radiations, which are most intensive at the middle IR-wavelength range, are recorded. Infrared dynamic thermal mapping methods, as described in Guljaev, Yu V, Godik, E. E. et al., "on the possibilities of the functional diagnostics of the biological subjects via their temporal dynamics of the infrared images," USSR Academy Nauk Proceedings/Biophysics, 1984, vol. 277, pp. 1486–1491, are based on such measurements. This method permits both measuring the tissue temperature with accuracy better than 0.1 degree and investigating the spatial-temporal distribution of blood microcirculation at the near surface tissues of the living organism. To accomplish this, temporal changes in the spatial distribution of IR-thermal radiation intensity of the living organism tissues are recorded, which provides the spatial-temporal microcirculation dynamics in these tissues. This method is used for investigation of both the spontaneous functional dynamics and functional dynamics initiated by the reactions of the physiological systems to different functional tests: reflective and humoral ones. The data thus obtained are represented in the form of the temporal sequences of the thermal images and/or the spatial-temporal cuts. Pain reactions, hyper- and hypo- ventilation and the effects of pharmaceutical treatments are able to be visualized under these conditions. In addition, this method reveals regions with various disturbances in the regulative mechanisms, and differential diagnostics of such disturbances can be performed. This method also permits estimating the state of the internal organs via the study of the spatial-temporal dynamics of the IR-radiation intensity recorded at the areas where the dermatomers reflectively connected with the corresponding organs are located.

However, the main disadvantage of the above described method is that it does not permit investigating the functional interconnection between various physiological processes which occur in a living organism under investigation. IR-thermal radiation provides information only about the dynamics of slow microcirculation, since the depth examined does not exceed 100 um. At the same time, the process of the thermal projection to the skin surface of the deeper layers of the blood flow network takes several seconds. For this reason, the above method does not permit investigating the fast blood flow dynamics connected, for example, with cardio and/or respiratory processes. The application of this method for the description of the living organism's functional state is restricted by information contained in the slow temporal dynamics of the skin surface temperature. In addition, this method fails to obtain the necessary set of additional physical parameters characterizing the functioning of the living organisms' investigated regions.

Another method of living organism functional diagnostics is a multichannel measurement of physiological parameters. A whole family of multichannel polygraphy is based on such approach, as described in Hasset, J,"Introduction into psycho-physiology," Moscow, Mir, 1981 (translated into Russian), for example. According to this method signals or information derived simultaneously from several channels are measured. The most complete set of information is represented by simultaneous measurements of the electroencephalogram, electrocardiogram, arterial pressure, skin electric resistance and/or skin galvanic reaction, skin temperature, plethysmogram and electromyogram, as described in, for example, Yoshihiro, Ito, "Autogenic training and treating apparatus," U.S. Pat. No. 4,573,472, March 1984. On the basis of the temporal dynamics of the recorded parameters, the living organism's functional state is judged. Recording of several different physiological signals gives a more accurate description of the organism's state.

At the same time, the multichannel polygraphy method reflects the temporal dynamics of the above parameters only at several discrete points of the organism and neither permits determination of the spatial distribution of the physiological reactions, i.e., the spatial portrait of the living organism's functioning, nor the investigation of the functional dynamics of the whole-organism's connectivity of the physiological systems.

A method of functional diagnostics based on multichannel mapping of the spatial-temporal distributions of the physical field tensions and radiation intensities of the human body (living organism) is also known, and described in Godik, E. E., Guljaev, Yu V. Human and animal physical fields, "V mire nauki" (Russian version of Scientific American), 1990, no. 5, pp. 74–83. This method is based on the following approach to determine the functional state of a living organism.

The human body or living organism, as a self-regulative system, is functionally inhomogeneous and non-stationary. For that reason its functioning and its multilevel regulative mechanisms are described by a hierarchy of rate constants from milliseconds to minutes, hours to days, etc. An adequate method of providing radio physical (electromagnetic) monitoring of such a system is called dynamic mapping, i.e., recording the temporal sequences of the instantaneous distributions (maps) of the physical fields tensions and/or radiation intensities over time intervals which are much less than the corresponding time constants of the regulative processes. The temporal map sequences thus obtained are called dynamic maps.

For example, to determine the tissue temperature of a living organism, its electromagnetic thermal radiation is recorded by means of infrared dynamic thermovision.

More specifically, a low intensity microwave thermal radiation comes from the organism's depth. Its brightness reflects non-inertially the functional dynamics of heat production and blood flow rate in the muscles, brain cortex and internal organs. Recording of such radiation is performed at wavelengths of about 3–30 cm, while the depth it comes from is of the order of 2–5 cm.

More detailed information about the spatial distribution of the thermal production functional dynamics inside the living organism is revealed by thermal acoustic radiation at an ultrasound frequency range of hundreds kilohertz to megahertz (corresponding to a wavelength of about 1 mm). Ultrasound waves, produced by thermal acoustic noise of the organism's tissues, come to the organism's surface from a greater depth (5–10 cm) and bring information, in real time scale, about functioning of the internal organs, such as the liver.

The organism's fast reflective regulation and functioning are revealed, in particular, in neural activity and in the muscular excitation processes. Information on these fast processes (the characteristic times are in the millisecond region) is revealed by a dynamic picture of the electrical potentials at the skin surface, and, especially, by the spatial-temporal dynamics of the magnetic fields around the body surface. Electric activity of the living organism's heart and brain are investigated by means of magnetic dynamic mapping.

Without illumination, extra weak radiation (chemoluminescence) of the skin covers connected with lipid peroxidation is observed in the optical yellow-green spectral range. Its intensity is determined by the antioxidizing status of the organism investigated. Under conditions of external illumination, the chemiluminescence intensity increases and, in addition, temporally and spectrally dynamic optical pictures appear at the near IR-wavelength range. It is the radiation back scattered by the biological tissues that produces this picture; it comes from the depth of up to one centimeter and characterizes the functional redistribution of the physiological pigments, especially various forms of blood hemoglobin.

In addition to the living organism's own physical fields and radiations, the organism's functional status is reflected in the external fields and radiations spatial-temporal dynamics, which are modulated as a result of the living organisms' physiological system's activity. Thus, blood redistribution related to cardiac pulsations is parametrically reflected in the geomagnetic field spatial-temporal dynamics near the torso, and the microcirculation dynamics of the capillary blood content is parametrically reflected by means of changes in the electrical tissue impedance. Electrical tissue impedance is measured by means of spatial-temporal distribution of external electrical fields having frequencies from tens to hundreds of kilohertz.

A considerable disadvantage of this latter method is that the dynamic maps provided by the measured parameters are considered separately. Furthermore, this method does not permit a comparison of variations in the spatial and temporal dynamics in different physical parameters which provide information on the state of different physiological systems and processes. In addition, this disadvantage relates equally to all the above described methods and noticeably limits their potential to reveal pathology.

A living organism's microwave thermal functional mapping by means of temporal sequences recording the organism's own microwave thermal radiation intensity spatial distributions and subsequently determining, on this basis, the distributions of integral depth temperature within the living organism's investigated areas is described in Godik, E. E., Guljaev, Yu V. A human body through the "Eyes of Radiophysics"—Radio Engineering (Russian), 1991, no. 8, pp. 51–61. English translation: Telecommunications and Radio Engineering, 1991, no. 9, pp. 90–99 and is based on recording the microwave brightness temperature distributions at the wavelength range of several centimeters and the subsequent analysis of the dynamics of the thermal field's behavior within the living organism's investigated area.

An apparatus for living organism microwave thermal functioning mapping is described by Guljaev, Yu V., Godik, E. E. et al. Radio thermal dynamic mapping of biological subjects, USSR Acad Nauk Dokl (Biophysics), 1988, 299, 1259–1253 (Russian) wherein a multichannel antenna system, connected to inputs of a high frequency radiometer, has the output connected with a multichannel analog-to-digital converter coupled to a personal computer. A common disadvantage of the above method and apparatus is the low information volume obtained, since these technical solutions permit estimating only spatial-temporal distributions of living organism thermal fields.

Other U.S. patents and applications of interest by the present inventor, Godik, are as follows: U.S. Pat. No. 5,865,167 entitled "Method of Living System Organism Diagnostics and Apparatus for its Realization"; U.S. Pat. No. 5,747,789 entitled "Method For Investigation of Distribution of Physiological Components in Human Body Tissues and Apparatus For its Realization"; U.S. Pat. No. 5,865,743 entitled "Method of Living Organism Multimodal Functional Mapping" (upon which this application claims priority); U.S. Pat. No. 5,730,133 entitled "Optical Functional Mamoscope"; U.S. Pat. No. 5,699,797 entitled "Method of Investigation of Microcirculation Functional Dynamics of Physiological Liquids in Skin and Apparatus for its Realization" and U.S. Pat. application Ser. No. 08/491,865 entitled "Method and Apparatus For Diagnostics of Internal Organs". All of the above being incorporated herein by reference.

It is therefore an object of this invention to provide complete information on the functional state of a living organism by the simultaneous measurement, analysis and evaluation of a set of independent parameters of physical fields and radiations.

It is another object of this invention to provide a method of multimodal functional mapping of a living organism by the interconnection of characteristics of the spatial-temporal dynamics of at least two parameters in order to diagnose the investigated organism.

SUMMARY OF THE INVENTION

The objects set forth above as well as further and other objects and advantages of the present invention are achieved by the embodiments of the invention described herein below.

A preferred embodiment of this invention is directed to recording the spatial-temporal distribution of at least one physical parameter and characterizing the physiological state of the living organism diagnosed. To determine the characteristics of the spatial-temporal distributions for each of the physical parameters, comparison is made with the characteristics recorded for the same living organism but at a different spatial area or at different time interval, or with similar characteristics obtained for another living organism. The results of such a comparison determine the functional state of the living organism diagnosed. In accordance with the invention, the spatial-temporal distribution of at least one physical parameter of the living organism diagnosed is recorded, and at least one interconnection characteristic of the spatial-temporal distributions of the recorded physical parameters is determined. The characteristics obtained are then compared with similar interconnection characteristics recorded for the same organism at different spatial or temporal ranges, or with similar characteristics of the same physical parameter recorded for another living organism. The results of such a comparison determine the functional state of the diagnosed living organism.

The above described procedure makes it possible to diagnose a living organism's state on the basis of an integral picture of the functional connectivity of physiological processes.

It is part of the inventive concept to record the spatial-temporal distributions of both a living organism's own physical field's tensions and radiation intensities as well as physical characteristics of its surface and external fields' tensions and/or intensities of external radiations, which are modulated due to the presence of another living organism. It is expedient, under these conditions, to record at least two such physical parameters simultaneously. Recording at least two parameters permits using the spatial-temporal dynamic characteristics of one of the physical parameters recorded for choosing the parameters for the other parameter recording: the beginning and the frequency of measurements and the necessary data volume. This helps to reduce the volume of the data analyzed and to simplify the means and equipment for the data accumulation. One parameter from the two simultaneously recorded parameters is used for synchronous accumulation and detection of the other parameter; this is especially useful for the non-invasive measurements of the above physical parameters under the conditions of low signal/noise ratio and at the presence of background disturbances.

Further, this invention divides the spatial-temporal distributions of each of the recorded physical parameters into the regions functionally connected with each other. This procedure permits the determination of the interconnection characteristics of the spatial-temporal distributions of these parameters. The interconnection characteristics provide information on the functioning of the diagnosed living organism's physiological systems and organs.

The elements of the integral spatial-temporal distribution of the recorded physical parameters could be used for investigation of the cross-correlation characteristics of the physiological processes for performing the analysis of their temporal delays and time scales, for revealing their spatial inhomogeneities and for obtaining other important data pertinent to the living organism functional diagnostics method.

More specifically, this invention provides a considerable increase in the information volume of the functional imaging due to simultaneous recording of one or more physical parameters reflecting the state of the physiological systems at the investigated region of the living organism, thus the name multimodal. In particular, by simultaneously recording the microwave thermal radiation and blood flow rate in the region investigated it is possible to separate thermal production changes connected with the cell metabolism and with local blood flow. In addition, the coefficients of optical radiation back scattering at the 0.3–2.0 um range are simultaneously recorded, the dependence of the picture obtained on the degree of the tissue blood content can also be estimated. In such a way, it is possible to determine the contributions made by different components to the integral picture of the organism thermal production changes, and thereby, to estimate the functional state of the living organism's separate systems.

The above mentioned technical result is achieved by modification of the known method of living organism functional mapping, determined by recording the temporal sequences of the intensity distributions of the living organism's own microwave thermal radiations and in determining on this basis the temporal sequences of the integral depth temperature distributions within the investigated region of the living organism. This involves additional synchronous measurements of the temporal sequences of the spatial distributions of at least one other physical parameter, reflecting the functional state of the living organism's investigated region biological tissues. The recording regime for one of the above physical parameters being optimized by taking into consideration important, from a physiological point of view, peculiarities of the spatial-temporal distribution of the other parameter. The functional state of the living organism's biological tissues is determined with the help of the spatial-temporal distribution of at least one of the parameters, characterizing a mutual radio between the physical parameters reflecting the biological tissue state.

As an additional physical parameter characterizing the biological tissue functional state, the following could be used: blood flow rate, skin surface temperature, the living organism's own magnetic field strength, the electric potential at the surface of the investigated area, the electric impedance of the biological tissues distributed over the depth of the living organism investigated area, the acousto-brightness temperature at the deep layers of living organism body, the acoustic impedance of the biological tissues at the depth of the living organism investigated area, the amplitude of the mechanical shifts of the living organism surface, or the coefficient of optical radiation back scattering from the near surface tissues of the living organism at 0.3–2.0 um wavelength range. Recording the above mentioned additional physical parameters can be performed together with microwave thermal mapping either separately or simultaneously with any number of the other aforementioned physical parameters in any combination.

Functionally connected areas of the investigated living organism can be mapped simultaneously both in the course of natural functional activity and/or when the organism is a subject of at least one external influence. As such an influence, physical, intellectual and/or emotional loading can be used, as well as taking a pharmacological preparation, or use of some sensor influence producing changes in the blood flow. The above listed external influences can be used both separately or in any combination with each other.

The above mentioned results can be achieved by a modification of a multichannel antenna-applicator system connected to inputs of a high frequency radiometer, whose outputs are coupled to a multichannel analog-to-digital converter connected with a personal computer, with the inclusion of at least one additional multichannel analyzer for measurements of at least one other physical parameter together with a commutator, with a group of the inputs of the latter being coupled to the radiometer outputs; the outputs of the latter being connected to the multichannel analog-to-digital converter inputs.

Meters of at least one additional analyzer can be integrated into a combined module with the dipoles of a multichannel antenna device.

The multimodal meter can switch on an antenna-applicator system arranged at the dielectric plane, a meter to measure surface temperature which is placed at the center of this system between the antenna dipole and on both sides of the surface temperature meter, symmetric relative to the antenna dipoles, a meter to measure the electric potential and input and output meters of an optical pulse-oxymeter.

For a better understanding of the present invention, together with other and further objects thereof, reference is made to the accompanying drawings and detailed description and its scope will be painted out in the appended claims.

DETAILED DESCRIPTION OF THE PREFERRED EMBODIMENT

Figure 1:
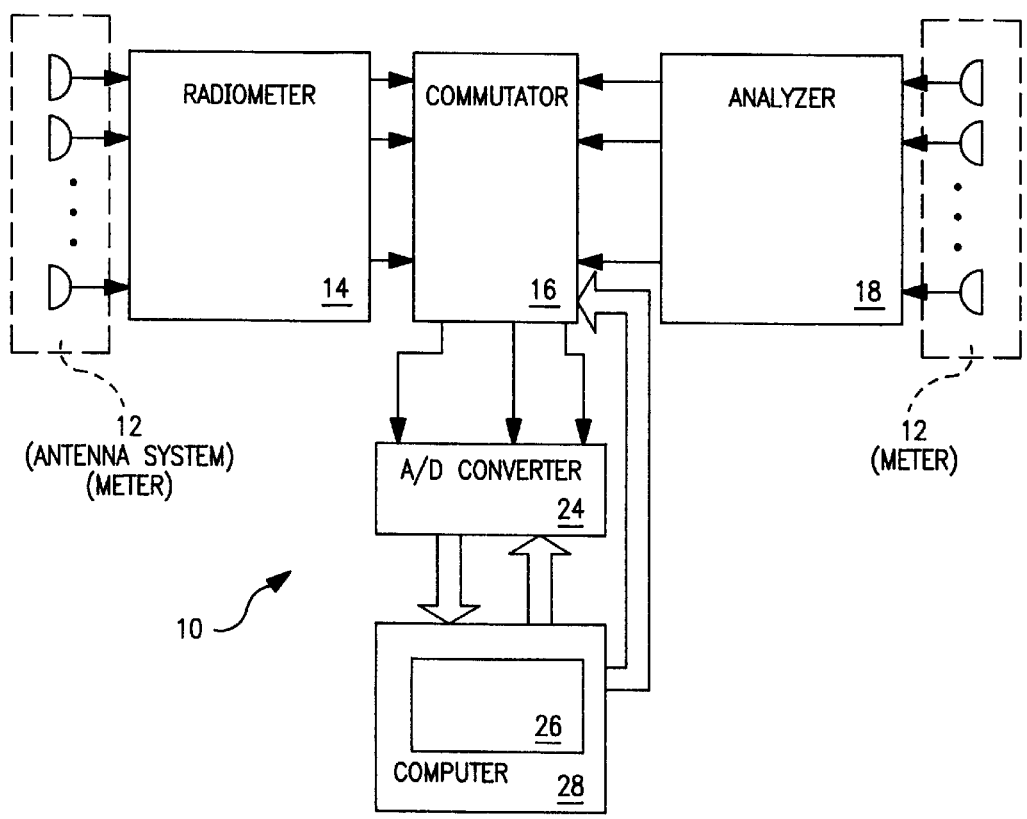
FIG. 1 is a general block diagram of an example of an apparatus utilized within this invention.

One aspect of the present invention involves recording the spatial-temporal distributions of one or several parameters (dynamic maps) of physical fields and radiations, providing information about physiological processes at (or near) the surface of the diagnosed living organism. Either simultaneously or after some time interval, the spatial-temporal distributions of one or several other parameters of the physical fields and radiations also at (or near) the same living organism's surface are measured.

The recorded parameters or measurements are the living organism's own physical fields' tensions and/or radiation intensities, as well as external fields' tensions and/or external radiations intensities changed as a result of the presence of the living organism investigated. Alternatively, the physical characteristics of another living organism's surface can be measured and combined with the above measurements. The first or higher order time and space derivatives of the physical parameters are often also recorded.

These spatial-temporal distributions of the physical parameters are called dynamic or functional maps and in case more aptly name multimodal functional maps.

The physical parameters depicted by the dynamic map by itself and, especially, the interconnection characteristics of the spatial-temporal dynamics parameters contain information on the functioning of the living organism's physiological systems. In order to determine the functional status of the living organism, the characteristics of the interconnection between several physical parameters are analyzed. In the simplest case, only two parameters are considered.

Of special importance while constructing the aforementioned functional or dynamic maps, is the analysis of the parameters' temporal behavior. Such analysis is performed by the comparison of the information elements of the parameters' dynamic maps, representing temporal behavior of the parameter at some spatial point or that averaged over some spatial area of the dynamic map. Sometimes, it is more convenient to use, as the information element of the parameter's dynamic map, a temporal regularity in the behavior of the histogram of the parameter amplitude at some fixed value of the latter. In particular, it is expedient to choose the parameters recorded so that they characterize different time scales in the living organism functional activity.

The analysis of the interconnection between the parameters dynamic maps makes it possible to reveal essential features of the whole-organism's spatial-temporal dynamics reflecting functional connectivity of the living organism's physiological processes which are responsible for the parameters recorded. The calculated interconnection characteristics give the quantitative estimations of these features.

The interconnection characteristics of the parameters' dynamic maps describe the temporal interconnection, the characteristic times, the mutual delays and the frequencies of the living organism's physiological processes. They permit determining the size and the characteristic scales of the physiological processes and, thereby, open up the possibility of the most complete description of the functional state of the living organism.

In order to perform the functional diagnosis of a living organism, dynamic maps of the physical parameters, as well as the corresponding interconnection characteristics, are obtained and are compared with similar dynamic maps of the parameters and their interconnection characteristics obtained from the same organism at another spatial area or for another time interval, or with those obtained for another living organism. With the results obtained from such a comparison, the multimodal functional state of the living organism is determined.

The interconnection characteristics of the physical parameters' dynamic maps permit an unambiguous determination of the functional state of the living organism at different time periods, even if some separate dynamic maps of the recorded parameters are coincident. The method of this invention for providing a functional diagnostics of a living organism's state makes it possible to determine both the functional status of the whole-organism's physiological systems and some of the separate systems and organs of the living organism investigated.

Examples of informative combinations of the recorded physical parameters are the following dynamic map combinations:

electric potential of the living organism's surface and the intensity of the microwave thermal radiation and/or the intensity of the acoustic radiation and/or infrared radiation intensity, the tension of magnetic field near the living organism's surface and the intensity of the microwave thermal radiation and/or the intensity of the acoustic radiation and/or electric potential of the living organism's surface, or spectral dependence of the coefficients of the optical radiation back scattered by the investigated area of the living organism and/or of that transmitted through this area, measured simultaneously at least at two wavelengths, and/or the intensity of the thermal infrared radiation and/or the intensities of the thermal acoustic radiations and/or microwave thermal radiation of the living organism and/or electrical potential on the surface and/or electrical impedance of the tissues and/or biomechanical parameters of the tissues.

The functional maps obtained are used for the formation of the characteristic images of the functional layers of the living organism differing by their depth: the skin, muscles, temperature core, etc. By means of the analysis of the characteristic images of these functional layers and taking into consideration the picture of the spatial-temporal distribution of the organism's functioning, the organism's functional status is determined. The characteristics of the spatial-temporal distribution of the functioning thus obtained are used as the feedback parameters when the living organism is the subject to the influence of some external sensor.

In a comparative analysis of the parameters' dynamic maps, especially when the calculation of their interconnection characteristics is performed, some elements of the initial information and a set of specific features for each of such elements are used. To calculate the interconnection characteristics, some digital measurements of the features' proximity are used. The information elements could be chosen independently for each of such maps under these conditions, or they could be chosen and constructed using the whole aggregate of the dynamic maps under the consideration.

The dynamic maps of several physical parameters are recorded simultaneously or with a time delay. The time delay being determined by the type of the physiological process investigated, the method of activation of these processes and by the physical characteristics of the tissues and organs of the living organism.

To activate physiological processes during the process of living organism functional diagnostics, some sensor influences and/or functional exercises are applied. For example, such influences include external temperature changes, changes in humidity, application of illumination, sound, mechanical influences, electric stimulation, alternating magnetic field or pharmacologic treatments. Functional exercises include some purposeful behavior of the living organism, for instance, muscle strain, hypo- and/or hyperventilation, intellectual loading, etc.

When at least two parameters are measured during the method of this invention in which simultaneous dynamic maps are recorded, one of the parameters could be used as a reference for the other. The features of the information elements of this reference parameter dynamic map are used, in real time or in a subsequent data treatment, for a synchronous and/or a pseudo-synchronous detection and data accumulation under conditions when periodical physiological processes are investigated. The reference parameter's features are used for a choice of the other parameter's recording regime and, in particular, for determination of the spatial scale and/or time frequency of the process of recording the dynamic maps for these latter parameters. Thereby, the conditions of the spatial-temporal continuity of the dynamic maps recorded for the investigated physiological process are obtained. The reference parameter features are used also for determination of the time intervals and spatial regions while recording the other parameters, thus permitting considerable reduction of the volume of the information processed.

As an information element of the dynamic map of the reference parameter, the parameter's temporal behavior at some spatial point, or averaged over some spatial region of the dynamic map, is used.

Sometimes, it is more convenient to use a twodimensional spatial distribution of the reference parameter at some definite moment or averaged over some period of time.

Functional diagnosis of the living organism's state based upon dynamic maps of the recorded parameters presumes determination of changes in the spatial areas, characteristic times and definite regularities in the recorded parameters in relation with one or another physiological process.

Recording of several parameters makes it possible to analyze the interconnection between the dynamic maps obtained for different parts of the living organism body, reflecting different stages in the development of the functional dynamics of the physiological processes. Such an analysis makes it possible to reveal the character of the functional connectivity both between different physiological systems (and/or organs) and inside them. In particular, the data obtained permits determination of the functional manifestations of different steps in the development of the physiological processes inside separate regions of the living organism.

Based upon the above, the dynamic maps of two or more parameters are divided into the areas functionally connected with each other. The dynamic maps of the first parameter are used for the clustering of the other parameter's dynamic maps and for the construction of the corresponding functional maps and vice versa. The functional maps of the parameters represent by itself functional images containing several clusters, each characterizing certain functional behavior The analysis of these functional maps for the living organism under diagnosis and the calculation, on the basis of such maps, of the characteristics of the functional interconnection between the physiological systems and processes yield information regarding the living organism's functional status.

Sometimes, the most important information about the functional connectivity is revealed by the rates of the parameter's temporal and/or spatial changes. Corresponding parameter derivatives determined by their dynamic maps serve as the information elements in such a case.

The analysis of the correlation between the information elements chosen and their features is performed for several parameters. In particular, functional maps are constructed reflecting the degree of the physiological processes manifestation, their rates and/or time delays. When it is necessary to analyze the synchronous functioning of different parts of the living organism, the parameter's functional maps are constructed on the basis of the cross-correlation between the selected elements of the parameter's dynamic maps. Of considerable interest for the analysis of the functional connectivity is the construction of the functional maps reflecting the qualitative similarity in the parameter's temporal behavior. This implies the construction of the areas with qualitatively similar dynamics, for example, the areas where an increase or a decrease (or some variation of such behavior) in the parameter's amplitude takes place.

For a more detailed description of the functional connectivity, the information elements of the dynamic maps of some parameters are expressed as a function of the information elements of the dynamic maps of the other parameters. The other method for functional map construction is decomposition of the information elements of some parameter's dynamic maps over some basis constructed by the information elements of the other parameter's dynamic maps. In particular, quite informative are the functional maps constructed with the use of the separation of the functional areas which are determined by a small number of factors connected with the physiological processes investigated.

To investigate the temporal-spatial distribution of the functions, spatial-temporal projections are created representing temporal distributions of the parameter's spatial changes over some chosen direction. This results in two-dimensional cuts of the parameters'dynamic maps being used as the information elements.

Spatial distribution of the functioning in the form of the corresponding functional maps is investigated by the analysis of the interconnection between the features of the information elements or some functions of these features. The construction of the functional (dynamic) maps presumes that the values of the features lie at some definite interval and that some logical terms are satisfied. The functional maps thus obtained contain information about the spatial scales of the physiological processes' functional manifestations of a similar type, about the presence of similar spatial shifts of the areas with maximal manifestation of the organism physiological processes, and about the waves and the spatial peculiarities in the functional dynamics.

To improve the reliability of the functional diagnosis of the living organism's state, the analysis of the functional connectivity of different physiological systems and organs is performed. Such an analysis permits analyzing the degree of the living organism's functional homogeneity under different conditions. For instance, changes in the spectral characteristics of the muscle's microtremor under the stress conditions are well known. Also, changes in correlation of the electric rhythms of the internal electric current generators are known to take place at different functional disturbances, etc. The method of this invention of living organism functional diagnostics makes it possible to reveal the absence or presence of the functional interconnection, to estimate the degree of this interconnection, to reveal the concealed interconnections between physiological processes, and to unravel the regularities in the functioning of the organism, on the basis of the integral spatial-temporal dynamics of the parameters recorded.

The analysis of the integral spatial-temporal dynamics of the parameters reveals the areas in the dynamic (functional) maps which are characterized by belonging to some definite class of the integral functional behaviors. Under these conditions, the main role is played not only by the similarity in the temporal dynamics or in the spatial distribution of the parameters in comparison with each other, as it was described above, but also by the interconnection of the parameter's spatial-temporal dynamics with some characteristics of the physiological processes. To obtain the clustering of the parameters' dynamic maps into different functional areas and to construct the functional maps, the characteristics of the spatial-temporal dynamics of the physiological processes used are obtained on the basis of some model description of the physiological processes.

In order to reveal the integral spatial dynamics at different areas of the living organism, the spatial distribution of the organism's functioning is analyzed. In this case, as information elements, integral spatial dynamics of changes in the value of the parameters along some chosen directions, or integral two-dimensional spatial distributions of the parameters at some fixed moment or that averaged over some time interval, or integral two-dimensional spatial-temporal distributions of the parameters at fixed values of one spatial coordinate or that averaged over some interval of changes in some of the spatial coordinates are chosen.

The compared features of the integral information elements utilized in the construction of the functional maps are the characteristics of the element amplitude, its spatial or temporal frequency or phase. Often the correlation between the features is analyzed by means of calculation of the pair cross-correlation coefficients. In more complicated cases, numerical measures of the qualitative similarity of the features of the integral elements are used, in order to compare the qualitative character of the integral dynamics of the parameters under consideration.

In the most complicated cases, a matrix of the paired distances of the features for all of the information elements under consideration and for all the dynamic maps of the recorded parameters are elaborated upon. On the basis of such a matrix, a set of the functional maps is constructed reflecting various aspects of the integral spatial-temporal dynamics of the parameters. It is possible, for example, to construct the hierarchy of the divisions into the functional areas relying upon the degree of the homogeneity in the functioning of the living organism investigated areas.

Sometimes, together with or instead of the spatial-temporal distributions of the organism's own physical parameters, similar distributions of an external sensor are recorded. Under these conditions, the characteristics of the integral spatial-temporal behavior of the recorded parameters are considered while performing the functional diagnostics.

Current physiological status of biological tissues is simultaneously reflected in a number of physical parameters, not just in any one of them; to be more accurate, it is the integral dynamics of a set of physical parameters reflecting the physiological state that gives the ability to judge this status. The intermodal parameters such as temporal delays in the value changes, spatial shifts of the activated areas, and the functions of mutual correlation, are of the primary importance in this respect. Thus, information indicated by microwave thermal radiation from the cell metabolism and local blood flow functional dynamics must be supplemented by information about the partial contribution to the picture observed from the local blood flow via the velocity distributions which could be estimated from the distribution of Doppler ultrasound waves frequency changes in the investigated region. Functional changes of the blood content are reflected in the dynamics of distribution of optical radiation back scattering coefficient at the near IR-wavelength range of 0.3–2.0 um, where biological tissues are known to be sufficiently transparent. The living organism's investigated region surface temperature distribution significantly supplements information from that gathered from a greater depth.

Information on the dynamics of deep temperatures of the biological tissues is indicated also by acoustic thermal radiation (biological tissues are transparent for ultrasound waves up to several centimeters at the frequencies of about 1 MHz or less). Due to fewer wavelengths of ultrasound waves at these frequencies (the wavelength in the order of a millimeter as compared with a decimeter for a microwave radiation with a similar depth of penetration), acoustic-thermal mapping permits realization of much better (up to several centimeters) spatial resolution. By simultaneous recording of changes in both the acoustic thermal and microwave thermal radiations, the deep temperature functional dynamics can be separated from the accompanying changes in the tissues' radiation coefficient produced by the blood content changes.

Simultaneous recording the dynamic distribution of the electric potential with the help of electroencephalography (EEG) and/or electromyography (EMG) at the surface of the investigated region permit synchronization with the process of the dynamic microwave thermal imaging.

Synchronous recording of Doppler frequency shifts of the ultrasound waves, together with the microwave thermal brightness temperature measurements, reveals information on the blood flow in the investigated region. This makes it possible to estimate a partial blood flow contribution to the overall thermal production of the living organism's investigated regional which is manifested in the depth microwave thermal brightness temperature.

Synchronous recording of the living organism's skin temperature together with the measurements of microwave thermal brightness temperature, as well as the acoustic thermal brightness temperature, give information on the thermal production of the tissue layers located deeper as compared with that brought by the microwave thermal brightness temperature. This permits determination of the temperature gradients from the skin surface to a greater depth, and also of estimating the depth at which the temperature anomaly is located by means of the temporal shifts in the dynamics of the surface and deep temperature changes.

If together with the measurements of the microwave thermal brightness temperature, the strength of the organism's own magnetic field and/or the value of electric potentials at the surface of the living organism's investigated area characterizing the degree of the tissue electrical activity are synchronously recorded, the energy expended necessary to produce the activation under the conditions of the current state bioelectrical excitability, i.e., some energy yield of the neuron network, can be estimated.

Synchronous with the measurements of microwave thermal brightness temperature, registration of the electric and acoustic impedance of the biological tissues or the coefficient of optical radiation back scattering at wavelength range of 0.7–2.0 um, yield information on the degree of the tissue blood content. This permits separating the functional dynamics of the depth temperature from the background of changes in the tissue radiation coefficient produced by their blood content changes. This is also used to estimate the partial contribution of the tissue blood content to the overall thermal production by the investigated region of the living organism.

Synchronously recording the amplitude, velocity and acceleration of the mechanical movements of the living organism's surface simultaneously with the microwave thermal brightness temperature measurements permits estimating the energy expenses which are necessary to produce the mechanical work, in particular muscle contraction.

Different sets of the parameters recorded should be selected depending upon which organ of the living organism is to be diagnosed. For example: for brain multimodal mapping, the set of parameters should include magnetic field and electric potential on the scalp to reflect brain cortex neuroelectric excitability; microwave and acoustic thermal radiation as a measure of brain temperature reflecting metabolic "payment" for the excitation; backscattered near infrared optical radiation for selected wavelengths carrying information on blood volume and oxygenation; and doppler ultrasound frequency shift, characterizing blood flow. For soft tissue organs with muscles (heart, skeletal muscles, arteries, stomach, intestines, bladder, uterus, etc.) additional parameters should be included such as biomechanical (see above) for reflecting the muscles' reactivity to neuroelectric excitation; electric and acoustic impedance for reflecting blood volume dynamics in the case of brain's diagnostics where the skull bone interferes with measuring such parameters for the brain cortex. For organs without muscles such as glands (breast, prostate, liver, etc.) that do not have intrinsic biomechanic activity parameters of tissue's biomechanical response to external compression compressibility could be very informative in addition to the parameters set forth above for skin diagnostics infrared thermal radiation for reflecting skin blood flow, and skin biomechanic deformation, reflecting blood volume dynamics, provides very valuable additional information to that of the parameters listed above.

Consequently, the process of simultaneously recording the dynamic images of several modalities (physical parameters) permits introducing a number of intermodal parameters, characterizing the state of the biological tissues, including:

Their amplitude ratios, describing the energy efficiency of the muscles mechanical work, of the neuron network electric activation, of the local blood flow changes, etc.

The temporal delay, describing the inertia properties of the muscles contraction, the perfusion rate at the capillary blood flow network, indicating a delay in the thermal production as compared with the bioelectric excitation of the muscle tissue.

The mutual spatial shifts of the dynamic maps of different modalities describing the functional connectivity of the living organism's various physiological processes, for example, the electric activity of the brain cortex and the physiological reactions of the skeleton muscles.

In addition, multimodal recording of physical parameters bringing information on the state of the physiological systems permits optimizing the parameters' recording regime for each of the modalities. For example, recording maps of the electric and magnetic fields permits decreasing considerably the number of radio-thermography meters needed only those regions of the electric and/or magnetic maps which manifest the greatest excitability can be utilized. An increase in the signal recording time produced by redistribution of the detection time at the regions of the greatest interest results in a considerable increase of the sensitivity of measurements.

The use of the relatively slow temporal dynamics of the acoustic-brightness and microwave thermal brightness temperature as a synchronous reference signal during the process of the electrical brain cortex imaging in the form of electric or magnetic maps permits considerable increase in the sensitivity of the signal separation from noise.

For example, functional mapping of the brain cortex of a patient undertaken while the patient is involved in some physical exercise with his arm was undertaken. Distribution of the microwave thermal brightness temperature at the decimeter wavelength range as well as distribution of the electroencephalogram bends were simultaneously recorded. Radio-thermograph and electroencephalograph meters were set up at the points on the head in accordance with the international system of electroencephalography procedures (known as scheme "10–20").

To increase the brain cortex response to the arm physical loading, a medical cuff was applied to compress the working arm. Physical loading of the arm under the conditions of muscle oxygen starvation due the artificially decreased blood flow was accompanied by an increased afferent pulsation of the somatomotor brain cortex.

Radio thermal and electric brain cortex maps were displayed on a personal computer monitor in pseudo color.

Soon after the cuff was applied to the left arm, a decrease in the thermal production of Roland furrow left somatomotor zone was recorded. After two minutes, the patient began performing physical exercises with his left arm for two minutes, and immediately after this, the area of an electric excitation appeared at the region of the right Roland furrow. This permitted switching off a part (3 from 12) of the radio thermograph antenna-applicators to increase the sensitivity via the rest of the channels, located at the region of the excitation without any increase in the measurements time. As a result, a delay in the excitation of the right Roland furrow (the temperature increase in it) was determined at the microwave thermal maps to be 1.5–2 minutes.

Thus, this experiment of the synchronous mapping of only two modalities reflecting the functional activation of the brain cortex (electric and thermal ones) permitted the recording of both the electric contralateral projection of the somatic influence to the somatomotor brain cortex and the energy "expenses" for the activation. In addition, ipso lateral vessel projection to the left Roland furrow was found (during medical cuff application).

The above procedure was performed with an apparatus 10 of the type shown in a block diagram in FIG. 1 of the drawings. This apparatus incorporates therein an antenna system 12 which includes, for example, a twelve wire vibrator antennae coupled to an electroencephalograph meter for detecting a first physical parameter. An ultrahigh frequency radiometer 14, operating in 38-cm wavelength range is coupled to antenna system 12 and commutator 16. Sensitivity to the fluctuations was 0.1 K during 1 s. As an additional analyzer 18, a 16-channel electroencephalograph was used. Analyzer 20 is coupled to a meter 20 to detect another physical parameter. The resultant information was input into a conventional personal computer 22 via commutator 16 and an analog-to-digital converter 24. Processed information was displayed at the computer monitor 26 in the form of temporal curves at each of the measuring points, and also in the form of thermal and electric maps of the brain cortex painted by pseudo colors in correspondence with the level of the value recorded.

Figure 2:
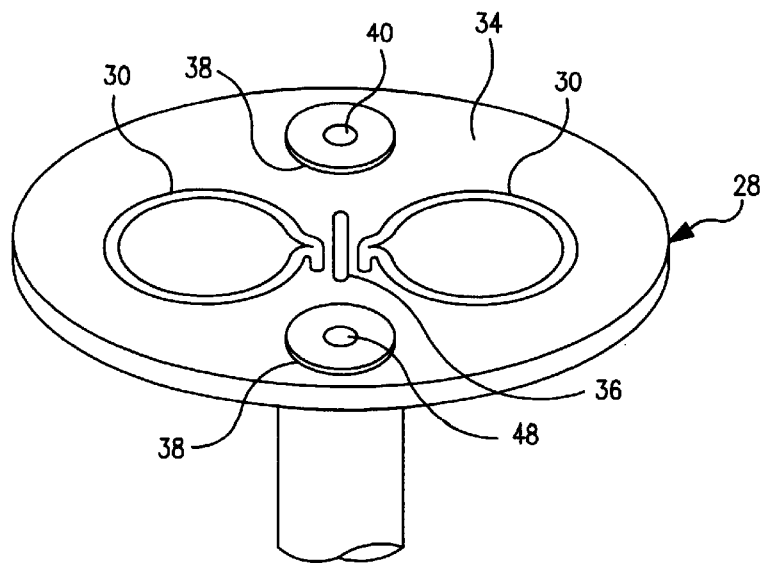
FIG. 2 is a pictorial, schematic representation of a multimodal meter utilized with this invention.

A multimodal meter 28 as shown in FIG. 2 was used for investigation of the functional state of muscles during physical loading. More specifically, multimodal meter 28 includes dipoles 30 of an antenna-applicator system arranged at the dielectric plane 34, meter 36 of the skin surface temperature, meters 38 of the electric potential, and also an IR-radiation source 40 and a detector 48. Under these conditions, the use of combined meters of a radio thermograph, a surface thermometer, an electromyograph and an optical pletismograph permits recording time delays in the development of different physiological processes in the muscles. As a reference point, the moment an electric excitation in the muscle appears following the arm physical loading, it is recorded by the electric maps. Then after a delay of several seconds, the muscle blood content changes, as recorded by the maps of distribution of the optical radiation back scattering coefficients at the hemoglobin absorption range. An increase in the microwave thermal brightness temperature takes place many seconds after the beginning of the arm loading, and the skin temperature changes appear with a delay of several minutes. The absolute values of the temporal delays depend on the patient and their current physical state. This permits estimating, in particular, the patient's cardiovascular system state.

Although the invention has been described with respect to various embodiments, it should be realized this invention is also capable of a wide variety of further and other embodiments within the spirit and scope of the appended claims.

I claim:

1. A method of diagnosing a living organism by multimodal functional mapping of the living organism, the method comprising the steps of:

selecting at least two parameters characterizing different modalities of physiological functioning of living tissues of said living organism;

obtaining said at least two parameters from substantially the same region of the living organism;

recording substantially simultaneously temporal sequences of said at least two parameters;

optimizing said recording of said temporal sequences of said at least two parameters by taking into consideration information obtained from said at least two parameters;

acquiring information about said temporal sequences of said at least two parameters from said recording;

analyzing said information in order to determine functional status information of the living organism;

generating from said functional status information at least one multimodal functional map of said region of the living organism; and diagnosing the condition of the living organism by analyzing said at least one multimodal functional map of the living organism.

2. The method of diagnosing a living organism as defined in claim 1 further comprising the step of applying at least one external influence to said living organism during recording of said at least two parameters.

3. The method of diagnosing a living organism as defined in claim 1 further comprising the step of selecting different sets of said recorded parameters depending upon which organ of the living organism is to be diagnosed.

4. A method of diagnosing a living organism by multimodal functional mapping of the living organism, the method comprising the steps of:

recording temporal sequences of a first physical parameter of the living organism reflecting one modality of a tissue's physiological functioning to be investigated;

recording substantially synchronously with said recording of said temporal sequences of said first parameter, temporal sequences of at least one additional physical parameter of the living organism reflective of another modality of said tissue's physiological functioning in said region of the living organism under investigation;

optimizing said recordings by taking into consideration information about said first and said at least one additional physical parameter of the living organism;

determining from said recordings of said temporal sequences of said first and said at least one additional physical parameters, at least one parameter characterizing an interconnection between said parameters of the living organism for said region under investigation;

providing said at least one multimodal function map representative of said at least one interconnection parameter characterizing intermodal functional conditions of said region of the living organism under investigation; and obtaining a diagnosis of said region of the living organism under investigation from said multimodal function map.

5. The method of diagnosing a living organism as defined in claim 4 wherein said first physical parameter represents thermal radiation intensity spatial-temporal distributions of said region of the living organism under investigation.

6. The method of diagnosing a living organism as defined in claim 4 further comprising the step of determining from said temporal sequences of said thermal radiation with different working intensity distributions for said tissue's physiological dynamics' for tissues temperature distributions at various depths within said region of the living organism under investigation.

7. The method of diagnosing a living organism as defined in claim 4 wherein said information obtained from one of said physical parameters is in the form of a doppler shift of frequency of ultrasound or electromagnetic waves, passing through the living tissue characterizing blood flow in said region under investigation.

8. The method of diagnosing a living organism as defined in claim 4 wherein said information obtained from one of said physical parameters is in the form of the living organism's skin surface temperature in said region under investigation.

9. The method of diagnosing a living organism as defined in claim 8 wherein said information of the living organism's skin temperature is derived from a spatial-temporal distribution of the skin's infrared thermal radiation.

10. The method of diagnosing a living organism as defined in claim 4 wherein said information obtained from one of said physical parameters is in the form of the living organism's magnetic field in said region under investigation.

11. The method of diagnosing a living organism as defined in claim 4 wherein said information obtained from one of said physical parameters is in the form of the living organism's skin surface electric potential in said region under investigation.

12. The method of diagnosing a living organism as defined in claim 4 wherein said information obtained from one of said physical parameters is in the form of the living organism's electric impedance in said region under investigation.

13. The method of diagnosing a living organism as defined in claim 4 wherein said information obtained from one of said physical parameters is in the form of the living organism's backscattered near infrared optical radiation near the surface in said region under investigation.

14. The method of diagnosing a living organism as defined in claim 4 wherein said information obtained from one of said physical parameters is in the form of the living organism's acoustic thermal radiation, thereby providing information on deep tissue temperature.

15. The method of diagnosing a living organism as defined in claim 4 wherein said information obtained from one of said physical parameters is in the form of acoustical impedance of said living tissue.

16. The method of diagnosing a living organism as defined in claim 4 wherein said information obtained from one of said physical parameters is in the form of at least one parameter of said tissue's biomechanics.

\* \* \* \* \*